United States Patent
Gostine

(10) Patent No.: US 10,124,021 B2
(45) Date of Patent: Nov. 13, 2018

(54) INTRAVENOUS FLUID

(71) Applicant: Andrew L. Gostine, Chicago, IL (US)

(72) Inventor: Andrew L. Gostine, Chicago, IL (US)

(*) Notice: Subject to any disclaimer, the term of this patent is extended or adjusted under 35 U.S.C. 154(b) by 0 days.

(21) Appl. No.: 15/443,054

(22) Filed: Feb. 27, 2017

(65) Prior Publication Data

US 2018/0177821 A1    Jun. 28, 2018

Related U.S. Application Data

(60) Provisional application No. 62/438,491, filed on Dec. 23, 2016.

(51) Int. Cl.

| | | |
|---|---|---|
| *A61K 33/00* | (2006.01) | |
| *A61K 9/00* | (2006.01) | |
| *A61K 9/08* | (2006.01) | |
| *A61K 33/20* | (2006.01) | |
| *A61K 31/19* | (2006.01) | |
| *A61K 31/191* | (2006.01) | |
| *A61K 33/06* | (2006.01) | |
| *A61K 47/02* | (2006.01) | |
| *A61K 47/12* | (2006.01) | |

(52) U.S. Cl.
CPC .......... *A61K 33/00* (2013.01); *A61K 9/0019* (2013.01); *A61K 9/08* (2013.01); *A61K 31/19* (2013.01); *A61K 31/191* (2013.01); *A61K 33/06* (2013.01); *A61K 33/20* (2013.01); *A61K 47/02* (2013.01); *A61K 47/12* (2013.01)

(58) Field of Classification Search
CPC ........ A61K 33/00; A61K 9/0019; A61K 9/08; A61K 31/19; A61K 31/191; A61K 33/06; A61K 33/20
USPC ........................................................ 424/663
See application file for complete search history.

(56) References Cited

U.S. PATENT DOCUMENTS

| | | | |
|---|---|---|---|
| 3,993,750 A | 11/1976 | Fox, Jr. | |
| 5,443,848 A | 8/1995 | Kramer et al. | |
| 2007/0135343 A1* | 6/2007 | Webb | A61K 9/0019 424/680 |
| 2008/0125488 A1* | 5/2008 | Leverve | A61K 31/19 514/557 |
| 2011/0189091 A1* | 8/2011 | Bachwich | A61K 9/08 424/9.1 |
| 2011/0318431 A1* | 12/2011 | Gulati | A61K 9/0019 424/681 |
| 2013/0274340 A1* | 10/2013 | Jeffs | A61K 9/0019 514/569 |

OTHER PUBLICATIONS

Liujiazi et al., Multiple Branch and Block Prediction. Hypertonic Saline for Brain Relaxation and Intracranial Pressure in Patients Undergoing Neurosurgical Procedures: A Meta-Analysis of Randomized [online],Jan. 30, 2015 [retrieved on Aug. 18, 2017]. Retrieved from the Internet:< URL:http://journals.plos.org/plosone/article?id=10.1371/journal.pone>.*
Strandvik, Anaesthesia, 2009,64, pp. 990-1003.*
Infusion Nurse Blog, Is there a difference? Osmolarity vs. Osmolality . . . [online],May 2010 [retrieved on Mar. 16, 2018]. Retrieved from the Internet:< https://infusionnurse.org/2010/05/14/osmolarity-vs-osmolality/>.*

* cited by examiner

*Primary Examiner* — Johann R Richter
*Assistant Examiner* — Courtney A Brown
(74) *Attorney, Agent, or Firm* — Butzel Long; Gunther J. Evanina

(57) ABSTRACT

Disclosed are intravenous hypertonic electrolyte solutions for treating intracranial hypertension while reducing the risk of inducing hyperchloremic metabolic acidosis. The solutions are characterized by a ratio of sodium-to-chloride (Na:Cl) ions of 1.2-1.6 and a total osmolarity of 310-400 mEq/L for a maintenance solution, and a total osmolarity greater than 1000 mEq/L for an initiation solution.

8 Claims, No Drawings

INTRAVENOUS FLUID

CROSS-REFERENCE TO RELATED APPLICATIONS

This application claims priority to U.S. Provisional Application No. 62/438,491, filed Dec. 23, 2016, which is incorporated herein by reference in its entirety.

FIELD OF THE DISCLOSURE

This disclosure relates to two, novel, intravenous (IV) fluid mixtures and a fluid builder kit for the treatment of patients at risk for or suffering from intracranial hypertension.

BACKGROUND OF THE DISCLOSURE

The brain is unique in that it is the only organ completely surrounded by bone. This establishes a fixed volume that limits the brain's ability to expand. Of the contents within the skull, 80% is occupied by brain tissue, 10% by cerebral spinal fluid (CSF), and 10% by blood. There are numerous injuries or pathological mechanisms that can predispose an individual to intracranial hypertension. Most commonly, this condition results from cerebral edema. Cerebral edema or brain swelling can be precipitated by strokes, tumors, traumatic brain injury, and bleeding ("insults"). Following these insults, the brain begins to swell and dispels first the CSF that serves to cushion the brain. Expansion beyond the space occupied by the CSF will start to reduce cerebral blood flow, leading to potentially permanent ischemic (oxygen deprivation) injury, or cause the brain itself to herniate across structures or through foramina (openings or orifices, as in bone tissue of the skull), resulting in death.

Over the years, medical professionals have developed devices (i.e. external ventricular drain) and therapies (i.e. steroids, hyperventilation, and hypertonic fluid) to help prevent and treat intracranial hypertension. One of the most routinely employed therapies is the use of hypertonic intravenous infusions (i.e. 3%, 7.5%, 10%, 23.4% saline or 20% mannitol). These infusions take advantage of the selectivity of the blood brain barrier, a semipermeable layer that tightly and slowly regulates the transfer of electrolytes in and out of the brain while allowing water to cross freely and rapidly via osmosis. By infusing solutions that are osmotically more concentrated than the brain's parenchyma (refer to Table 1), providers can remove water from the brain tissue and deliver it to the blood where it can be eliminated via the kidneys, in the form of urine, or by dialysis.

The above treatment is essentially a two-step process. Water must be drawn out of the brain and then eliminated from the body. Thus, the ideal fluid therapy must at a minimum be more osmotically concentrated than blood and brain tissue, but non-toxic to the kidneys. Current IV fluids consist of various hypertonic sodium chloride solutions or 20% mannitol. However, all of these fluids are capable of causing profound electrolyte abnormalities and acute renal failure, which are counterproductive in the management of cerebral edema.

For example, 3% saline solution has a total osmolarity of 1026 mEq/L and is made from equal parts sodium and chloride (513 mEq/L of each). This fluid is often used to rapidly increase the total serum and sodium osmolarity of the patient's blood (FIG. 1). Following this relatively rapid alteration, providers will use intermittent or continuous infusions and frequent laboratory evaluation to maintain and monitor, respectively, the desired sodium and serum osmolarity goals. Ultimately, the utilization of any hypertonic saline will cause a greater perturbation in the patient's chloride level than the sodium level. Normal serum chloride concentrations are about 104 mEq/L±5 mEq/L while sodium levels are about 140 mEq/L±5 mEq/L. Thus, other things being equal, the infusion of a solution that is equal parts sodium and chloride will cause a larger proportional increase in the patient's chloride level than the sodium level at equilibrium.

The more profound proportional increase in serum chloride concentration has many notable effects. The decrease in the proportional difference between sodium and chloride, due to the greater increase in chloride relative to sodium, results in a hyperchloremic metabolic acidosis due to a reduction in the strong ion difference. As the patient's blood becomes more acidemic, numerous systems are affected. Perhaps most concerning, however, is that acidemia can cause cerebral vascular dilation, potentially increasing the volume of blood and the overall pressure within the skull. Compared to balanced intravenous fluids, saline formulations case greater hemodynamic instability, a reduced cardiac index, a more altered microcirculation, and more severe organ dysfunction (Orbegozo, D., MD, Effects of Different Crystalloid Solutions on Hemodynamics, Peripheral Perfusion, and the Microcirculation in Experimental Abdominal sepsis; Anesthesiology 10, 2016, Vol. 125, pages 744-754).

Compared to the rest of the body's organs and capillary beds, the renal vasculature is tightly controlled by the serum chloride level (Wilcox, C S, Regulation of renal blood flow by plasma chloride; J. Clin. Invest., 1983, March; 71(3); pages 726-735). Increases in serum chloride concentrations can cause significant reductions in renal blood flow in a dose dependent manner. There are few physiologic and pathologic conditions that cause elevations in a patient's serum chloride level as those seen with hypertonic saline. Combined with the fluid restriction that frequently follows the initiation of hypertonic therapy (as current maintenance fluids are all hypotonic relative to frequently prescribed hyperosmolar goals), the hyperchloremic state puts the patient at an increased risk for acute kidney dysfunction and injury, which can greatly complicate the management of intracranial hypertension.

Based on the aforementioned discussion, there is a need for improved intravenous (IV) fluid mixtures for the treatment of patients at risk for or suffering from intracranial hypertension which reduce the risks associated with hyperchloremic metabolic acidosis. All current therapies require that physicians balance the risks of administering suboptimal IV fluids with the benefits of reducing brain swelling.

SUMMARY OF THE DISCLOSURE

Disclosed are two different hypertonic electrolyte solutions, each composed of a potential range of various electrolytes having a ratio of sodium-to-chloride from 1.2-1.6 mEq/L. The total osmolarity of a first or initiation solution is greater than or equal to 1000 mEq/L. A second solution to maintain euvolemia within the new hyperosmolar environment has a total osmolarity from about 310 mEq/L to about 400 mEq/L. The electrolyte solutions can increase the patient's total serum and sodium level while causing much smaller increases in serum chloride to prevent acidosis and reduced renal blood flow.

DESCRIPTION OF THE PREFERRED EMBODIMENTS

These and other objects, advantages, purposes and features of the present invention will become apparent upon review of the following specification in conjunction with the drawings.

Two new electrolyte solutions, or more accurately a range of new electrolyte solutions, are designed to eliminate the harms associated with current IV fluid therapies by increasing the patient's total serum osmolarity and sodium level, while reducing the observed increase in serum chloride that is observed with hypertonic saline and which causes acidosis and reduced renal blood flow. This new "balanced, hypertonic fluid" is unique in its ratio of sodium to chloride. The fluids have a range of possible electrolyte concentrations so long as the ratio of sodium-to-chloride is from 1.2 to 1.6. For example, the ratio of sodium-to-chloride for either the initial treatment solution or the maintenance solution can be 1.3-1.5 or 1.35-1.45. The electrolyte solution allows medical providers to treat cerebral edema with a markedly reduced risk for hyperchloremia, acidosis, renal injury and hypovolemia.

A hyperosmolar solution for initiation therapy can be composed of a mixture of volumes from 10% saline (3422 mEq/L), 8.4% sodium bicarbonate (2000 mEq/L) and 3% potassium chloride (800 mEq/L) though other component solutions are possible reagents. The set of possible initiation solutions has a total osmolarity greater than 1000 mEq/L, e.g., 1500-3000 mEq/L or 2000-2800 mEq/L. One example of this initiation therapy has the constituent concentrations listed in Table 1.

TABLE 1

Example of IV Fluid Electrolyte Concentrations for Initiation Therapy

|  | Gostine's Initiate |  |
|---|---|---|
| Substrate |  |  |
| Sodium | 1315.5 | mEq/L |
| Potassium | 16 | mEq/L |
| Chloride | 871.5 | mEq/L |
| Bicarbonate | 460 | mEq/L |
| Total Osmolarity | 2663 | mEq/L |
| Fluid Builder |  |  |
| Vol of 8.4% NaHCO3 Added | 230 | mL |
| Vol of 10% NaCl Added | 250 | mL |
| Vol of 3% KCl Added | 20 | mL |

Of note, in this example solution (Gostine's Initiate), the sodium-to-chloride ratio is about 1.51 and the total osmolarity is about 2663 mEq/L. All percentages herein are by weight unless otherwise indicated.

The new maintenance therapy solution for the maintenance of euvolemia in hyperosmolar states has a sodium-to-chloride ratio from 1.2 to 1.6 and a total osmolarity from about 310 mEq/L to about 400 mEq/L. The solution can be prepared by adding 8.4% sodium bicarbonate (NaHCO$_3$), 10% saline (NaCl), and 50% magnesium sulfate (MgSO$_4$) to an existing electrolytic infusion fluid having the following constituent concentrations in water: Sodium=about 140 mEq/L, Potassium=about 5 mEq/L, Chloride=about 98 mEq/L, Bicarbonate=about 0 mEq/L, Magnesium=about 3 mEq/L, Acetate=about 27 mEq/L, and Gluconate=about 23 mEq/L, with a total osmolarity of about 294 mEq/L. Sufficient 8.4% sodium bicarbonate, 10% saline and 50% magnesium sulfate solutions are added to the existing electrolytic infusion fluid to achieve the new electrolyte ranges in solution having the constituent concentrations (though other combinations exist that meet the aforementioned sodium-to-chloride ratio and total osmolarity criteria) listed in the preceding paragraph and also in the right-hand column of Table 2.

TABLE 2

Physiologic and IV Fluid Electrolyte Concentrations for existing and the novel Maintenance Therapy

| Electrolyte | Normal Blood | 0.9% Saline | Plasma-Lyte A ® | Gostine's Elevate |  |
|---|---|---|---|---|---|
| Sodium | 140 ± 5 | 154 | 140 | 145-185 | mEq/L |
| Potassium | 4.3 ± 0.7 | 0 | 5 | 4-5 | mEq/L |
| Chloride | 104 ± 5 | 154 | 98 | 96-135 | mEq/L |
| Bicarbonate | 24 ± 2 | 0 | 0 | 0-11 | mEq/L |
| Magnesium | 2.4 ± 0.6 | 0 | 3 | 2-11 | mEq/L |
| Calcium | 9.3 ± 0.8 | 0 | 0 | 0 | mEq/L |
| Acetate | 0 | 0 | 27 | 26-27 | mEq/L |
| Gluconate | 0 | 0 | 23 | 22-23 | mEq/L |
| Total Osmolarity | 280-300 | 308 | 296 | 310-400 | mEq/L |
| Fluid Builder |  |  |  |  |  |
| Vol of 8.4% NaHCO3 Added |  |  |  | 20-0 | mL |
| Vol of 10% NaCl Added |  |  |  | 40-0 | mL |
| Vol of 50% MgSO4 Added |  |  |  | 5-0 | mL |

As an example, the new maintenance electrolyte solution can have the following ranges of concentrations of constituents, expressed as milliequivalents per liter (mEq/L), which will allow it to satisfy the requirements of a sodium-to-chloride ratio between 1.2 and 1.6 and a total osmolarity between 310 and 400 mEq/L: Sodium=about 145 to 185 mEq/L, Potassium=about 5 to 4 mEq/L, Chloride=about 96 to 135 mEq/L, Bicarbonate=about 0 to 11 mEq/L, Magnesium=about 11 to 2 mEq/L, Acetate=about 27 to 26 mEq/L, and Gluconate=about 23 to 22 mEq/L, resulting in a total osmolarity of at least 310 to about 400 mEq/L. The new electrolyte solution may be devoid of Calcium. The range of the concentrations found in the maintenance therapy is also reflected in the right-hand column of Table 2 (under "Gostine's Elevate"), which also lists, for comparison, the physiologic and IV fluid electrolyte concentrations of normal blood, 0.9% saline, and PLASMA-LYTE A available from Baxter International Inc. of Deerfield, Ill.

For the maintenance therapy solution, it will be appreciated that when sodium bicarbonate, saline, or magnesium sulfate are added to an existing electrolyte solution there will be a drop of the osmolarity for the constituents found only in the existing electrolytic infusion fluid, as reflected in the above numbers. Some reductions in osmolarity are less clearly reflected because of rounding, and it will be appreciated that concentrations of constituents found only in the existing electrolytic infusion fluid will be minimally affected by the introduction of 8.4% sodium bicarbonate solution, 10% saline, or 50% magnesium sulfate, of which only about 0 to 60 mL of each may be added to an approximately 1,000 mL container of existing electrolytic infusion fluid to achieve the new electrolytic infusion fluid.

It will further be appreciated that the new electrolytic infusion fluid may be created using a kit containing multiple small "doses" of 8.4% sodium bicarbonate, 10% saline and 50% magnesium sulfate solutions to be added to a container of existing electrolytic infusion fluid having known volume and concentration. Such kits would allow medical professionals to select a desired concentration of electrolytes and total osmolality for the solution in the new electrolytic fluid, hence the example ranges listed in Table 2.

The resulting new electrolytic infusion fluids provides a mixture containing an appropriate balance of negative and positive ions in solution, without excessively raising chloride concentration, to provide an increased osmolarity (compared to known infusion fluids) that results in therapeutic effect on cerebral edema by reducing water content in the brain, and without causing kidney damage, acidosis or hypovolemia.

The electrolytic infusion fluids described herein are used by first intravenously administering the disclosed initiation solution to a patient in need of treatment of intracranial hypertension, and thereafter, optionally intravenously administering to the patient the disclosed maintenance solution. Treatments may be repeated as deemed appropriate.

Changes and modifications in the specifically-described embodiments may be carried out without departing from the principles of the present invention, which is intended to be limited only by the scope of the appended claims as interpreted according to the principles of patent law including the doctrine of equivalents.

What is claimed is:

1. An intravenous infusion fluid for initial treatment of intracranial hypertension, comprising:
   an aqueous hyperosmolar solution having a sodium-to-chloride ratio of 1.2-1.6 and a total electrolyte concentration greater than 1000 mEq/L.

2. The fluid of claim 1 formulated for initial therapy in which the sodium is present at a concentration of about 950 to 1500 mEq/L;
   the chloride is present at a concentration of about 350 to 1400 mEq/L;
   the intravenous infusion fluid further comprises potassium and bicarbonate, wherein the bicarbonate is present at a concentration of about 150 to 800 mEq/L; and
   the potassium is present at a concentration of about 0 to 70 mEq/L.

3. An intravenous infusion fluid for maintenance treatment of intracranial hypertension, comprising:
   an aqueous hyperosmolar solution having a sodium-to-chloride ratio of 1.2-1.6 and a total electrolyte concentration of 310-400 mEq/L, in which the sodium is present at a concentration of about 145 to 185 mEq/L;
   the chloride is present at a concentration of about 96 to 135 mEq/L;
   the intravenous infusion fluid further comprises bicarbonate, magnesium, acetate, gluconate and potassium, wherein
   the bicarbonate is present at a concentration of about 0 to 11 mEq/L;
   the magnesium is present at a concentration of about 2 to 11 mEq/L;
   the acetate is present at a concentration of about 26 to 27 mEq/L;
   the gluconate is present at a concentration of about 22 to 23 mEq/L; and
   the potassium is present at a concentration of from about 4 to 5 mEq/L.

4. The fluid of claim 1, wherein the sodium-to-chloride ratio is 1.3-1.5.

5. The fluid of claim 1, wherein the sodium-to-chloride ratio is 1.35-1.45.

6. The fluid of claim 1, wherein the total electrolyte concentration is 1500-3000 mEq/L.

7. The fluid of claim 1, wherein the total electrolyte concentration is 2000-2800 mEq/L.

8. A kit for modifying an existing electrolyte fluid to reduce the proportional of chloride relative to sodium, comprising:
   multiple vials each containing sodium bicarbonate, sodium chloride and magnesium sulfate in amounts that provide a higher sodium concentration than chloride concentration, wherein the concentration of sodium bicarbonate is 8.4%, the concentration of sodium chloride is 10%, and the concentration of magnesium sulfate is 50%.

* * * * *